United States Patent [19]
Laszlovszky et al.

[11] Patent Number: 6,103,724
[45] Date of Patent: Aug. 15, 2000

[54] 2-METHOXYPHENYLPIPERAZINE DERIVATIVES

[75] Inventors: Istvan Laszlovszky; Gyorgy Domany; Tibor Acs; Gyorgy Ferenczy; Csaba Szantay; Eszter Thuroczyne Kalman; Erzsebet Lapis; Ferenc Trischler; Bela Hegedus; Feranc Auth; Monika Csejtei; Egon Karpati; Bela Kiss; Judit Laszy; Margit Pellioniszne Paroczai; Adam Sarkadi; Sandor Szabo, all of Budapest, Hungary

[73] Assignee: Richter Gedeon Vegyeszeti Gyar Rt., Budapest, Hungary

[21] Appl. No.: 09/284,313

[22] PCT Filed: Oct. 22, 1997

[86] PCT No.: PCT/HU97/00069

§ 371 Date: Apr. 27, 1999

§ 102(e) Date: Apr. 27, 1999

[87] PCT Pub. No.: WO98/18797

PCT Pub. Date: May 7, 1998

[30] Foreign Application Priority Data

Oct. 30, 1996 [HU] Hungary .................................. 9603001

[51] Int. Cl.[7] ..................... A61K 31/496; A61K 31/519; C07D 471/04; C07D 487/04; C07D 513/04
[52] U.S. Cl. ........................... 514/253; 544/281; 544/362; 544/368
[58] Field of Search .................................. 544/281, 362, 544/368; 514/253

[56] References Cited

U.S. PATENT DOCUMENTS

| 4,880,824 | 11/1989 | Press et al. | 514/368 |
| 5,688,949 | 11/1997 | Inoue et al. | 544/281 |
| 6,013,654 | 1/2000 | TenBrink | 514/300 |

FOREIGN PATENT DOCUMENTS

WO 95/30659  11/1995  WIPO.

OTHER PUBLICATIONS

VanTol et al. *Nature*, vol. 350, pp. 610–614, (1991).

Saxena, *Pharmac. Ther.* vol. 66, pp. 339–368, (1995).

"Discovery of Selective Dopamine D3 Ligands" by Jon Wright et al. published in Bioorganic & Medicinal Chemistry Letters, vol. 5, No. 21, 1995.

J. Med. Chem. 1988, 31, 2221–2227; P.J. Sanfilippo; Syntheses of (Aryloxy) alkylamines.

*Primary Examiner*—Emily Bernhardt
*Attorney, Agent, or Firm*—Herbert Dubno

[57] ABSTRACT

The invention relates to fused heterocyclic compounds with ring junction nitrogen atom of the formula:

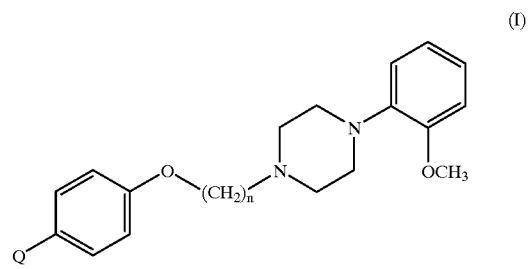

wherein Q stands for 2-indolizinyl, 2-imidazo[1,2-a]pyridinyl, 2-imidazo[1,2-a]pyrimidinyl, 6-(2,3-dihydroimidazo[2,1-b]thiazol)-yl or 6-imidazo[2,1-b]thiazolyl group; and n is an integer from 2 to 4, as well as therapeutically useful salts thereof. The invention further relates to pharmaceutical compositions containing these compounds as well as a process for the preparation of the above compounds and compositions. The compounds of formula (I) exhibit mainly antipsychotic effects so the invention relates also to a method of treatment of schizophrenia, organic mental disorders, affective disorders, anxiety and personality disorders.

7 Claims, No Drawings

2-METHOXYPHENYLPIPERAZINE DERIVATIVES

The invention relates to novel fused heterocyclic compounds with ring junction nitrogen atom of a general formula (I)

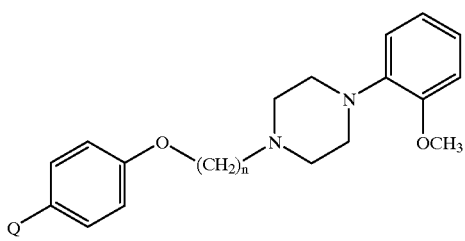

(I)

wherein

Q stands for 2-indolizinyl, 2-imidazo[1,2-a]pyridinyl, 2-imidazo[1,2-a]-pyrimidinyl, 6-(2,3-dihydroimidazo[2,1-b]thiazol)-yl or 6-imidazo[2,1-b]-thiazolyl group; and n is an integer from 2 to 4, and to their therapeutically useful salts and pharmaceutical compositions containing these compounds. Furthermore, the invention relates also to a process for the preparation of the compounds of formula (I) and their therapeutically useful salts in such a way that a haloalkyl ether derivative of formula (II)

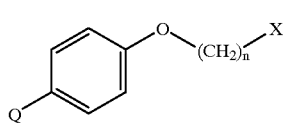

(II)

wherein Q and n are as defined above, and X means halogen is reacted with (2-methoxyphenyl)piperazine of formula (III).

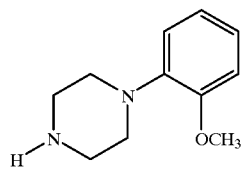

(III)

The compounds of formula (I) according to the invention are novel and possess significant biological activity, first of all antipsychotic effects.

The invention relates also to a method of treatment, which comprises administering a therapeutically active amount of a compound of formula (I) or a therapeutically acceptable salt thereof to a patient to be treated.

Among the starting substances, some of chloroalkyl ether derivatives of formula (II) are known from the literature, such as 3-[4-(2-imidazo[1,2-a]pyridinyl) -phenoxy]propyl chlorid, 3-[4-(2-imidazo[1,2-a]pyrimidinyl)phenoxy]propyl chloride, or 3-[4-(6-imidazo[2,1-b]thiazolyl)phenoxy] propyl chloride [J. Med. Chem. 31, 2221 (1988)]. Other starting substances of formula (II) can be obtained according to the preparation process described in the above-cited literature.

(2-Methoxyphenyl)piperazine of formula (III) is a known, commercially available substance.

Compounds structurally similar to the substances of formula (I) are known from the literature. Such (substituted amino)propoxyphenylimidazo[1,2-a]pyridines, substituted amino)propoxyphenylimidazo[1,2-a]pyrimidines and (substituted amino)propoxyphenylimidazo[2,1-b]thiazoles are described in the above-cited publication [J. Med. Chem. 31, 2221 (1988)], however, unlike the compounds according to the invention, these compounds possess calcium channel-blocking and local anaesthetic effects.

In contrast to the structurally closely related compounds known from the literature, the novel compounds of formula (I) according to the invention are orally effective and are endowed of a considerable neuroleptic activitiy. Based on their biological activity, these compounds can be used as atypical antipsychotics, antidepressants, anxiolytics, neuroprotective and/or cognitive function improving agents, antiemetics or antiaddictives.

Since the 70's, antipsychotics have successfully been employed for the treatment of schizophrenia. Up to the present haloperidol has been used in the clinical practice most widely. Phenothiazines and haloperidol played a pioneering role in this therapeutic field and considerably contributed to the development of the dopamine theory of schizophrenia. Later researches confirmed also the role of serotonine and a number of other neurotransmitter systems, such as histaminerg, α-adrenerg, CCK-erg, etc. in this disorder. However, haloperidol and other typical antipsychotics improve only the positive symptoms of the disease, e. g. hallucinations, delusions, agitation and thought disturbances, whereas negative symptoms, such as emotional obtusion, autism, social isolation, neglection of personal hygiene remain unimproved. In addition, nearly 30% of the patients do not respond to the treatment and a number of undesired adverse effects cannot be excluded, either. From these, the most severe adverse effects are the appearance of extrapyramidal symptoms (EPS), because of the strong but not regionselective antagonism of D-2 dopamine receptor, deterioration of cognitive functions caused by anticholinergic effect, orthostatic hypotonia (α-adrenerg antagonism), and hyperprolactinaemia.

Nowadays, intensive research is being devoted to atypical antipsichotics, which are capable of improving both positive and negative symptoms, do not induce extrapyramidal symptoms or only in doses higher than therapeutical, only a few non-responsive patients should be taken into account at all if any and other side effects are also negligible. Clozapine, if did not cause agranulocytosis, could be such an ideal antipsychotic.

Nowadays research is being focused on discovering clozapine-like atypical antipsychotics. Clozapine-like action means that the molecule possesses a strong antipsychotic effect without appearance of the above side effects. Such compounds have a direct or indirect selective action on the dopaminergic pathways of limbo brain and this effect is associated with a complex receptor profile. Within the complex receptor profile, the D-2 receptor antagonistic effect characteristic of haloperidol is not dominant.

The novel compounds of formula (I) according to the invention exert an antispychotic effect similar to that of the atypical antipsychotic clozapin. Both antipsychotic and oral activites of the compounds were confirmed by a pomorphine-induced climbing and sniffing tests in vivo. The mechanism of action of the compounds was characterized by receptor binding tests in vitro.

Inhibition of apomorphine (APO) induced climbing and sniffing

CD-1 (Charles River) male mice weighing 22 to 24 g were pretreated with 1% Tween 80 solution of the compound to be tested. After 55 minutes, the animals were placed two by two into examination cages [P. Potrais et al.: Psychopharmacol 50, 1-6 (1976)]. Six animals were used in each group. At 60 minutes after pretreatment, the animals were treated subcutaneously with 1 mg/kg of apomorphine (APO). From the 10th to 25th minute following APO treatment the animals were scored in each minute as follows: 0: all the four Q: A means 2-indolizinyl, Q: B means 2-imidazo[1,2-a]pyridinyl, Q: C means 2-imidazo[1,2-a]pyrimidinyl, Q: D means 6-(2,3-dihydroimidazo[2,1-b]thiazol)-yl and Q: E means 6-imidazo[2,1-b]thiazolyl group.

TABLE 1

| Compound No. | Q | n | ED$_{50}$ (mg/kg p.o.) | | Sniff./ Climb. | Receptor IC$_{50}$ (nM) | | |
|---|---|---|---|---|---|---|---|---|
| | | | Inhibition of APO-induced climbing | Inhibition of APO-induced sniffing | | D-2 | 5-HT1A | α-1 |
| 4510407 | A | 2 | >>30 | — | — | 258 | 802 | 542 |
| 4510423 | A | 3 | 4.1 | >10 | >2.4 | 77 | 1000 | 359 |
| 4510613 | A | 4 | 14.8 | >30 | >2.0 | 99 | 243 | 842 |
| 4510408 | B | 2 | 2.4 | ≈10 | 4.1 | 56 | 70 | 36 |
| 4510067 | B | 3 | 7.2 | 16.2 | 2.3 | 17 | 202 | 57 |
| 4510915 | B | 4 | 10.7 | — | — | 69 | 21 | 34 |
| 4510411 | C | 2 | 3.4 | >>30 | >8.8 | 133 | 10 | 63 |
| 4510424 | C | 3 | 8.9 | >>30 | 3.4 | 34 | 66 | 30 |
| 4510645 | C | 4 | 20.5 | >>30 | >1.5 | 55 | 12 | 22 |
| 4510471 | D | 2 | 6.3 | >>30 | 4.8 | 117 | 29 | 75 |
| 4510473 | D | 3 | 15.3 | >30 | >2.0 | 29 | 122 | 48 |
| 4510991 | D | 4 | ≈30 | >>30 | >1.0 | 56 | 9 | 16 |
| 4510470 | E | 2 | 0.8 | 4.5 | 5.6 | 73 | 38 | 101 |
| 4510472 | E | 3 | 3.4 | ≈10 | 2.9 | 23 | 96 | 56 |
| 4510916 | E | 4 | 6.1 | ≈30 | >4.9 | 55 | 8 | 28 |
| haloperidol | | | 0.19 | 0.4 | 2.1 | 3 | 3860 | 19 |
| clozapine | | | 3.3 | 12.3 | 3.7 | 159 | 647 | 35 | legs of the animal are on the ground; 1: the animal climbs on the grid by its both forelegs; 2: the animal climbs on the grid by all its four legs. The inhibitory effect was related to the APO control group, which could achieve 32 scores as a maximum.

The inhibition of APO-induced sniffing stereotypy was measured simultaneously with the inhibition of climbing from the 10th to 25th minute following the APO administration according to S. Gerhardt [S. Gerhardt et al.: Life Sci. 37, 2355–2363 (1985)].

Receptor binding assays

D-2

Binding to the D-2 dopamine receptor was studied according to P. Seeman [P. Seeman et al.: J. Neurochem. 43, 221–235 (1984)] by using 0.5 nM $^3$H-spiperone as ligand; the non-specific binding was determined in the presence of 10 μM(±)-sulphide.

5-HT1A

Determination of the 5-HT1A subtype of serotonin receptor was carried out by a modification [M. D. Hall et al.: J. Neurochem. 44, 1685–1696 (1985); H. Gozlan et al.: Nature 305, 140–142 (1983)] of the method described by Peroutka [S. J. Peroutka: J. Neurochem.47, 529–540 (1986)]. 0.5 nM $^3$H-8-OH-DPAT was used as ligand, where non-specific binding was determined by using 10 μM serotonin.

Alpha-1

The α-1 receptor activity of the compounds was measured according to the method of Greengrass and Horung [P. Greengrass et al.: Eur. J. Pharmacol 55, 323–326 (1979); R. Horung et al.: Naunyn-Schmiedeb. Arch Pharmacol. 308, 223–230 (1979)] by using $^3$H-prazosin as ligand. The non-specific binding was measured with 10 μM (±)-phentolamine.

The results of the in vivo and in vitro investigations are summarized in Table 1, where It is evident from the ED$_{50}$ values of inhibition of the APO-induced climbing inhibition shown in Table 1 that most of the compounds inhibit the APO-induced climbing already in a low oral dose (0.8–10 mg/kg), a result supporting the in vivo antipsychotic activity of the compounds. The most active compound No. 4510470 is of ten-fold oral activity as compared to clozapine, but several other molecules, such as the compounds Nos. 4510408, 4510411 or 4510472, have ED$_{50}$ values lower than or equal to that of clozapine. Simultaneously, the apomorphine-induced stereotypy measured by the occurrence of sniffing in this case was prevented only in significantly higher doses usually above 30 mg/kg of the compounds according to the invention. The above results, including the sniffing/climbing ratio, confirm the compounds' limbic selectivity in vivo and this selectivity is better than that of clozapine. Based on the limbic selectivity, the action of the compounds is similar to that of atypical antipsychotics, thus, the occurrence of extrapyramidal symptoms (EPS) cannot be expected or only in higher doses.

The mechanism of action based on results of receptor binding assays shown in Table 1. provide further support to the atypical antipsychotic nature of the compounds of the invention. Thus, their D-2 dopamine receptor activity is less marked than the effect of the typical antipsychotic haloperidol (3 nM) and indicates similarity rather to the atypical antipsychotic clozapine. However, the compounds according to the invention are somewhat more effective on this receptor subtype. Their clozapine-like α-adrenerg receptor activity provides further evidence for their atypical features. The compounds in general as well as their representatives, such as molecules No. 4510916 and No. 4510991, exert especially strong activity on 5-HT1A receptor subtypes. This effect is significantly different from the weak 5-HT1A receptor activity of clozapine and similarly, it is different from the strength of activity of other atypical antispychotics which have been commercially available up to the present.

This difference is even more markedly expressed by the D-2/5-HT1A ratio. For example, this ratio is 0.2 for clozapine, whereas it is 1.9 for the compound No. 4510470 and is even 6.9 for the compound No. 4510916. The 5-HT1A receptor activity indicates also an anxiolytic effect component of the compounds.

In summary: the novel compounds of the invention are atypical antipsychotics, which are essentially more active than clozapine after oral administration. Similarly to clozapine, they possess a complex receptor profile, however, receptor subtypes and their strength of activity involved participating in the mechanism of action of the compounds are different from those of clozapine. Thus, the compounds of the invention are endowed of other character and new sort of complex profile of mechanism of action. Therefore, the compounds according to the invention could be very effective in the treatment of acute and chronic schizophrenia; paranoia and other psychotic disturbances; organic mental disorders, such as delirium, dementia. withdrawal syndromes, addictions, mental retardation, tic disorders; affective disorders, such as mania, bipolar disorders, cyclothymia, dysthymia; anxiety disorders, including panic disorders, phobia, obsessive-compulsive disorders, generalized anxiety syndrome and personality disorders, such as compulsive, paranoid, schizoid, antisocial and any other disorders related to psychomotor agitation. The expected therapeutical doses of the compounds are between 0.01 and 50 mg/kg of body weight, once or in repeated subdoses daily, administered orally, intraperitoneally or subcutaneously route.

The preparation of the novel compounds of formula (I) according to the invention are hereinafter described in detail.

The haloalkyl ether derivatives of formula (III), preferably 2-chloroalkyl ether derivative known from the literature or prepared by known methods, are reacted with the similarly known (2-methoxyphenyl)piperazin or a salt thereof, preferably with the commercially available (2-methoxyphenyl)piperazin dihydrochloride in an organic protic solvent, e.g. in an alcohol or in any organic dipolar-aprotic solvent, such as an aliphatic ketone; or acetonitrile, dimethylformamide and the like, optionally in the presence of a base and an alkaline metal iodide, such as sodium iodide. Suitable bases are inorganic bases, e.g. potassium carbonate, sodium carbonate; or organic bases, e.g. triethylamine. The reaction is carried out at the boiling point of the solvent used, for a reaction time of 5 to 10 hours. After evaporation of the reaction mixture containing the compound of formula (I), treating the dry residue with water and extracting the obtained mixture with a water-immiscible solvent, the crude target compound of formula (I) is obtained, which can be purified by recrystallization if necessary.

If desired, the compounds of formula (I) can be converted to their acid addition salts in a manner known per se.

The salt formation is accomplished in a known manner in an inert organic solvent or solvent mixture in such a way that the compound of formula (I) is dissolved in the selected solvent and subsequently, the appropriate acid is added in portions to the above solution until the mixture becomes strongly acidic (about pH 1 value). Alternatively, the salt formation can be performed by adding the solution of the acid in the calculated amount in the selected solvents to the above solution. Thereafter, the precipitated acid addition salt is separated from the reaction mixture in a suitable manner, e.g. by filtration.

The active ingredient of formula (I) can be transformed to pharmaceutical compositions by mixing it with nontoxic, inert solid or liquid carriers commonly used in the therapy for parenteral or enteral administration. E.g. water, gelatin, lactose, starch, pectin, magnesium stearate, stearic acid, talc, vegetable oils such as olive oil or peanut oil and the like are useful carriers. The active ingredient may be formulated in the form of usual pharmaceutical compositions, particularly in solid form, e.g. as tablets, dragees, capsules, pills, suppository and the like. The amount of the solid carrier may be varied within wide limits, preferably between about 25 mg and 1 g. These compositions may optionally contain the commonly used pharmaceutical auxiliaries (additives), e.g. preservatives, stabilizing, wetting, emulsifying agents or the like. The preparation of these compositions can be accomplished by common methods, e.g. by sieving, mixing, granulating and then compressing the components in the case of solid compositions. The compositions may be exposed to further usual operations, e.g. sterilization.

The invention is illustrated in detail by the following non-limiting examples.

EXAMPLE 1

1-(2-Methoxyphenyl)-4-{2-[4-(2-indolizinyl) phenoxy]ethyl}piperazine

[Formula (I), Q=2-indolizinyl, n=2]

A mixture containing 2.72 g (10 mmol) of 2-[4-(2-indolizinyl)phenoxy]ethyl chloride, 2.74 g (12 mmol) of (2-methoxyphenyl)piperazine dihydrochloride, 2.54 g (24 mmol) of sodium carbonate, 0.3 g (2 mmol) of anhydrous sodium iodide and 40 ml of methyl isobutyl ketone is boiled under reflux for 10 hours. After evaporating the solvent under reduced pressure, the residue is thoroughly triturated with 20 ml of water, then extracted with 80 ml of chloroform. The organic phase is twice washed with 15 ml of water each, dried over anhydrous sodium sulfate and the drying agent is filtered off. The filtrate is stirred with 1 g of charcoal and 0.5 g of aluminium oxide for 20 minutes, then filtered and evaporated to its half volume under reduced pressure. After adding 40 ml of ethanol to the residue, it is evaporated to about 15 ml under reduced pressure. The precipitated material is filtered and dried. The obtained 2.9 g crude product is dissolved in 30 ml of chloroform, 30 ml of ethanol are added then, the solution obtained is evaporated to about 15 ml under reduced pressure. After filtering and drying the precipitated substance, the title compound is obtained in a yield of 2.61 g (61%), m.p.: 159–161° C.

EXAMPLE 2

1-(2-Methoxyphenyl)-4-{3-[4-(2-indolizinyl) phenoxy]propyl}piperazine

[Formula (I), Q=2-indolizinyl, n=3]

The procedure described in Example 1 is followed, except that 3-[4-(2-indolizinyl)phenoxy]propyl chloride is used as starting material instead of 2-[4-(2-indolizinyl)phenoxy] ethyl chloride. The title compound melts at 157–158° C.

EXAMPLE 3

1-(2-Methoxyphenyl)-4-{4-[4-(2-indolizinyl) phenoxy]butyl}piperazine

[Formula (I), Q=2-indolizinyl, n=4], compound No. 4510613

The procedure described in Example 1 is followed, except that 4-[4-(2-indolizinyl)phenoxy]butyl chloride is used as starting material instead of 2-[4-(2-indolizinyl)phenoxy] ethyl chloride. The title compound melts at 153–155° C.

EXAMPLE 4

1-(2-Methoxyphenyl)-4-{2-[4-(2-imidazo[1,2-a] pyridinyl)phenoxy]ethyl}piperazine

[Formula (I), Q=2-imidazo[1,2-a]pyridinyl, n=2], compound No. 4510408

The procedure described in Example 1 is followed, except that 2-[4-(2-imidazo[1,2-a]pyridinyl)phenoxy]ethyl chloride is used as starting material instead of 2-[4-(2-indolizinyl)phenoxy]ethyl chloride. The title compound melts at 151–153° C.

EXAMPLE 5

1-(2-Methoxyphenyl)-4-{3-[4-(2-imidazo[1,2-a]pyridinyl)phenoxy]propyl}piperazine

[Formula (I), Q=2-imidazo[1,2-a]pyridinyl, n=3], compound No. 4510067

The procedure described in Example 1 is followed, except that 3-[4-(2-imidazo[1,2-a]pyridinyl)phenoxy]propyl chloride is used as starting material instead of 2-[4-(2-indolizinyl)phenoxy]ethyl chloride. The title compound melts at 149–150° C.

EXAMPLE 6

1-(2-Methoxyphenyl)-4-{4-[4-(2-imidazo[1,2-a]pyridinyl)phenoxy]butyl}piperazine

[Formula (I), Q=2-imidazo[1,2-a]pyridinyl, n=4], compound No. 4510915

The procedure described in Example 1 is followed, except that 4-[4-(2-imidazo[1,2-a]pyridinyl)phenoxy]butyl chloride is used as starting material instead of 2-[4-(2-indolizinyl)phenoxy]ethyl chloride. The title compound melts at 144–145° C.

EXAMPLE 7

1-(2-Methoxyphenyl)-4-{2-[4-(2-imidazo[1,2-a]pyrimidinyl)phenoxy]ethyl}piperazine

[Formula (I), Q=2-imidazo[1,2-a]pyrimidinyl, n=2], compound No.4510911

The procedure described in Example 1 is followed, except that 2-[4-(2-imidazo[1,2-a]pyrimidinyl)phenoxy]ethyl chloride is used as starting material instead of 2-[4-(2-indolizinyl)phenoxy]ethyl chloride. The title compound melts at 150–152° C.

EXAMPLE 8

1-(2-Methoxyphenyl)-4-{3-[4-(2-imidazo[1,2-a]pyrimidinyl)phenoxy]propyl}piperazine

[Formula(I), Q=2-imidazo[1,2-a]pyrimidinyl, n=3], compound No. 4510924

The procedure described in Example 1 is followed, except that 3-[4-(2-imidazo[1,2-a]pyrimidinyl)phenoxy]propyl chloride is used as starting material instead of 2-[4-(2-indolizinyl)phenoxy]ethyl chloride. The title compound melts at 156–158° C.

EXAMPLE 9

1-(2-Methoxyphenyl)-4-{4-[4-(2-imidazo[1,2-a]pyrimidinyl)phenoxy]butyl}piperazine

[Formula(I), Q=2-imidazo[1,2-a]pyrimidinyl, n=4], compound No. 4510645

The procedure described in Example 1 is followed, except that 4-[4-(2-imidazo[1,2-a]pyrimidinyl)phenoxy]butyl chloride is used as starting material instead of 2-[4-(2-indolizinyl)phenoxy]ethyl chloride. The title compound melts at 151–153° C.

EXAMPLE 10

1-(2-Methoxyphenyl)-4-{2-[4-[6-(2,3-dihydroimidazo[2,1-b]thiazol)yl)phenoxy]ethyl}piperazine

[Formula (I), Q=6-(2,3-dihydroimidazo[2,1-b]thiazol)yl, n=2],

The procedure described in Example 1 is followed, except that 2-{4-[6-(2,3-dihydroimidazo[2,1-b]thiazol)yl]phenoxy}ethtyl} chlorid is used as starting material instead of 2-[4-(2-indolizinyl)phenoxy]ethyl chloride. The title compound melts at 145–147° C.

EXAMPLE 11

1-(2-Methoxyphenyl)-4-{3-[4-[6-(2,3-dihydroimidazo[2,1-b]thiazol)yl]phenoxy]propyl}piperazine

[Formula (I), Q=6-(2,3-dihydroimidazo[2,1-b]thiazol)yl, n=3], compound No.4510473

The procedure described in Example 1 is followed, except that 3-{4-[6-(2,3-dihydroimidazo[2,1-b]thiazol)-yl]phenoxy}propyl chlorid is used as starting material instead of 2-[4-(2-indolizinyl)phenoxy]ethyl chloride. The title compound melts at 142–144° C.

EXAMPLE 12

1-(2-Methoxyphenyl)-4-{4-[4-[6-(2,3-dihydroimidazo[2,1-b]thiazol)-yl]phenoxy]butyl}piperazine

[Formula (I), Q=6-(2,3-dihydroimidazo[2,1-b]thiazol)-yl, n=4], compound No. 4510991

The procedure described in Example 1 is followed, except that 4-{4-[6-(2,3-dihydroimidazo[2,1-b]thiazol)-yl]phenoxy}butyl chlorid is used as starting material instead of 2-[4-(2-indolizinyl)phenoxy]ethyl chloride. The title compound melts at 139–140° C.

EXAMPLE 13

1-(2-Methoxyphenyl)-4-{2-[4-[6-(imidazo[2,1-b]thiazolyl]phenoxy]ethyl}piperazine

[Formula (I), Q=6-imidazo[2,1-b]thiazolyl, n=2],

The procedure described in Example 1 is followed, except that 2-{4-[6-imidazo[2,1-b]thiazolyl]phenoxy}ethtyl chlorid is used as starting material instead of 2-[4-(2-indolizinyl)phenoxy]ethyl chloride. The title compound melts at 158–161° C.

EXAMPLE 14

1-(2-Methoxyphenyl)-4-{3-[4-[6-imidazo[2,1-b]thiazolyl)phenoxy]propyl}piperazine

[Formula (I), Q=6-imidazo[2,1-b]thiazolyl, n=3], compound No. 4510472

The procedure described in Example 1 is followed, except that 3-[4-(6-imidazo[2,1-b]thiazolyl)phenoxy]propyl chloride is used as starting material instead of 2-[4-(2-indolizinyl)phenoxy]ethyl chloride. The title compound melts at 130–132° C.

EXAMPLE 15

1-(2-Methoxyphenyl)-4-{4-[4-[6-imidazo[2,1-b]thiazolyl)phenoxy]butyl}piperazine

[Formula (I), Q=6-imidazo[2,1-b]thiazolyl, n=4]

The procedure described in Example 1 is followed, except that 4-[4-[6-imidazo[2,1-b]thiazolyl)phenoxy]butyl chloride is used as starting material instead of 2-[4-(2-indolizinyl)phenoxy]ethyl chloride. The title compound melts at 128–130° C.

EXAMPLE 16

1-(2-Methoxyphenyl)-4-{2-[4-(2-indolizinyl)phenoxy]ethyl}piperazine dihydrochloride

[Formula (I), Q=2-indolizinyl, n=2], compound No. 4510407

After dissolving 21.5 g (0.05 mol) of 1-(2-methodyphenyl)-4-{2-[4-(2-indolizinyl)phenoxy]ethyl piperazine (prepared as described in Example 1) in 50 ml of chloroform, 50 ml of ethanol are added to the solution, then the reaction mixture is acidified to pH 1 by adding 20 to 30% ethanolic hydrochloric acid. The precipitate is filtered, washed with a little amount of ethanol and dried to yield 24.5 g (98%) of title compound, m.p. 220–222° C.

EXAMPLE 17

1-(2-Methoxyphenyl)-4-{3-[4-[2-indolizinyl) phenoxy]propyl}piperazine dihydrochloride

[Formula (I), Q=2-indolizinyl, n=3], compound No. 4510423

The procedure described in Example 16 is followed, except that 1-(2-methoxyphenyl)-4-{3-[4-(2-indolizinyl) phenyoxy]propyl}piperazine is used as starting substance instead of 1-(2-methoxyphenyl)-4-{2-[4-(2-indolizinyl) phenoxy]ethyl}piperazine. The title compound melts at 239–241° C.

EXAMPLE 18

1-(2-Methoxyphenyl)-4-{2-[4-[6-(2,3-dihydroimidazo[2,1-b]thiazol)-yl]phenoxy] ethyl}piperazine trihydrochloride

[Formula (I), Q=6-(2,3-dihydroimidazo[2,1-b]thiazol)-yl, n=2], compound No. 4510471

The procedure described in Example 16 is followed, except that 1-(2-methoxyphenyl)-4-{2-[4-(6-(2,3-dihydroimidazo[2,1-b]thiazol)-yl]phenoxy}ethyl piperazine is used as starting substance instead of 1-(2-methoxyphenyl)-4-{2-[4-(2-indolizinyl)phenoxy] jethyl}piperazine. The title compound melts at 214–216° C.

EXAMPLE 19

1-(2-Methoxyphenyl)-4-{2-[4-[6-imidazo[2,1-b] thiazolyl]phenoxy]ethyl}piperazine trihydrochloride

[Formula (I), Q=6-imidazo[2,1-b]thiazolyl, n=2], compound No. 4510470

The procedure described in Example 16 is followed, except that 1-(2-methoxyphenyl)-4-{2-[4-(6-imidazol[2,1-b]thiazolyl]phenoxy]ethyl}piperazine is used as starting material instead of 1-(2-methoxyphenyl)-4-{2-[4-(2-indolizinyl) phenoxy]ethyl}piperazine. The title compound melts at 254–256° C.

EXAMPLE 20

1-(2-Methoxyphenyl)4-{4-[4-[6-imidazo[2,1-b] thiazolyl]phenoxy]butyl}piperazine trihydrochloride

[Formula (I), Q=6-imidazo[2,1-b]thiazolyl, n=4], compound No. 4510916

The procedure described in Example 16 is followed, except that 1-(2-methoxyphenyl)-4-{4-[4-(6-imidazol[2,1-b]thiazolyl]phenoxy]ethyl}piperazine is used as starting material instead of 1-(2-methoxyphenyl)-4-{2-[4-(2-indolizinyl)phenoxy]ethyl}piperazine. The title compound melts at 227–229° C.

What is claimed is:

1. A compound of the Formula (I)

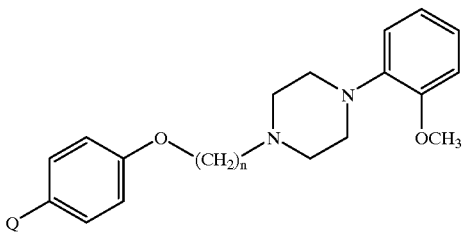

wherein

Q is 2-indolizinyl, 2-imidazo{1,2-a}pyridinyl, 2-imidazo{1,2-a}pyrimidinyl, 6-(2,3-dihydroimidazo [2,1-b]thiazol)-yl or 6-imidazo{2,1-b}thiazol)-yl; and n is an integer of 2 to 4; or a therapeutically acceptable salt thereof.

2. The compound of the Formula (I) defined in defined in claim 1 wherein Q is 2-imidazo{1,2-a}pyridinyl or 6-imidazo{2,1-b}thiazol)-yl or a therapeutically acceptable salt thereof.

3. The compound of the Formula (I) defined in claim 1 selected from the group consisting of:

(a) 1-(2-methoxyphenyl)-4-{2-[4-(6-imidazo{2,1-b}thiazolyl)phenoxy]ethyl} piperazine;

(b) 1-(2-methoxyphenyl)-4-{2-[4-(2-imidazo{1,2-a}pyridinyl)phenoxy]ethyl} piperazine;

(c) 1-(2-methoxyphenyl)-4-{4-[4-(6-(2,3-dihydroimidazo{2,1-b}thiazol)-yl)phenoxy]butyl} piperazine;

(d) 1-(2-methoxyphenyl)-4-{3-{4-(6-imidazo{2,1-b}thiazolyl)phenoxy]propyl} piperazine;

(e) 1-(2-methoxyphenyl)-4-{4-[4-(6-imidazo{2,1-b}thiazol)-yl)phenoxy]butyl} piperazine; and (f) 1-(2-methoxyphenyl)-4-{(2-[4-(2-imidazo{1,2-a}pyrimidinyl)phenoxy]ethyl} piperazine, or a therapeutically is acceptable salt thereof as defined in claim 1.

4. A pharmaceutical composition for treating a psychosis which comprises as active ingredient, a therapeutically effective amount of the compound of the Formula (I) defined in claim 1 or a therapeutically acceptable salt thereof.

5. A process for preparing a compound of the Formula (I):

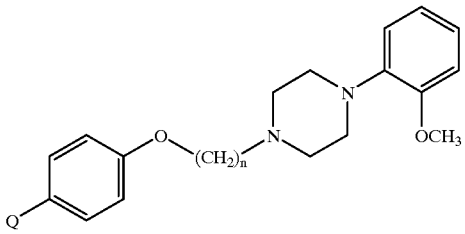

wherein

Q is 2-indolizinyl, 2-imidazo{1,2-a}pyridinyl, 2-imidazo{1,2-a}pyrimidinyl, 6-(2,3-dihydroimidazo [2,1-b]thiazol)-yl or 6-imidazo{2,1-b}thiazol)-yl; or a pharmaceutically acceptable salt thereof, and n is an integer from 2 to 4, which comprises the step of N-alkylating a compound of the Formula (III)

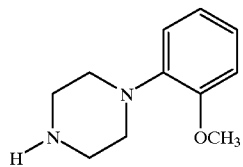

or a salt thereof with a compound of the Formula (II)

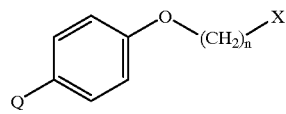

wherein X is halogen in an organic solvent, to obtain the compound of the Formula (I) and where a therapeutically acceptable salt of the Formula (I) is desired converting the compound of the Formula (I) to a therapeutically acceptable salt.

6. The process for preparing a compound of the Formula (I) defined in claim 5 wherein the N-alkylation of the compound of the Formula (III) with the compound of the Formula (II) is carried out in the presence of an alkali iodide.

7. A method of treating a psychosis in a patient which comprises the step of administering to said patient, a therapeutically effective amount of the compound of the Formula (I) defined in claim 1 or a therapeutically acceptable salt thereof.

* * * * *